United States Patent
Gleich et al.

(10) Patent No.: US 12,007,291 B2
(45) Date of Patent: Jun. 11, 2024

(54) PRESSURE SENSING UNIT, SYSTEM AND METHOD FOR REMOTE PRESSURE SENSING

(71) Applicant: KONINKLIJKE PHILIPS N.V., Eindhoven (NL)

(72) Inventors: Bernhard Gleich, Hamburg (DE); Jürgen Erwin Rahmer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 454 days.

(21) Appl. No.: 17/250,141

(22) PCT Filed: Jun. 11, 2019

(86) PCT No.: PCT/EP2019/065090
§ 371 (c)(1),
(2) Date: Dec. 7, 2020

(87) PCT Pub. No.: WO2019/243098
PCT Pub. Date: Dec. 26, 2019

(65) Prior Publication Data
US 2021/0244305 A1      Aug. 12, 2021

(30) Foreign Application Priority Data
Jun. 20, 2018   (EP) .................................... 18178783

(51) Int. Cl.
*G01K 7/36* (2006.01)
*A61B 1/00* (2006.01)
(Continued)

(52) U.S. Cl.
CPC ............ *G01K 7/36* (2013.01); *A61B 1/00158* (2013.01); *A61B 5/0215* (2013.01);
(Continued)

(58) Field of Classification Search
CPC .......... A61B 5/6852; A61B 2562/0223; A61B 5/0215; A61B 5/05; A61B 5/6851;
(Continued)

(56) References Cited

U.S. PATENT DOCUMENTS

| 3,456,508 A | 7/1969 | Frische |
| 4,044,283 A * | 8/1977 | Allison .................. G02B 26/10 318/128 |

(Continued)

FOREIGN PATENT DOCUMENTS

| EP | 0172268 | 2/1986 |
| GB | 626624 | 7/1949 |
| JP | 2001242024 A | 9/2001 |

OTHER PUBLICATIONS

International Search Report and Written Opinion dated Aug. 26, 2019 For International Application No. PCT/EP2019/065090 Filed Jun. 11, 2019.
(Continued)

*Primary Examiner* — Oommen Jacob
(74) *Attorney, Agent, or Firm* — Sherry Austin

(57) ABSTRACT

A wireless pressure sensing unit (20) comprises a membrane (25) forming an outer wall portion of a cavity and two permanent magnets (26,28) inside the cavity. One magnet is coupled to the membrane, and at least one magnet is free to oscillate with a rotational movement. At least one is free to oscillate with a rotational movement. The oscillation takes place at a resonance frequency, which is a function of the sensed pressure, which pressure influences the spacing between the two permanent magnets. This oscillation frequency can be sensed remotely by measuring a magnetic field altered by the oscillation. The wireless pressure sensing unit may be provided on a catheter (21) or guidewire.

20 Claims, 3 Drawing Sheets

(51) Int. Cl.
    *A61B 5/00*          (2006.01)
    *A61B 5/0215*      (2006.01)
    *A61B 5/05*          (2021.01)
    *A61B 5/06*          (2006.01)
    *A61B 34/20*        (2016.01)
    *A61B 90/00*        (2016.01)
    *G01K 1/26*          (2006.01)
    *G01K 13/04*        (2006.01)
    *G01L 9/00*          (2006.01)

(52) U.S. Cl.
    CPC ............ *A61B 5/02152* (2013.01); *A61B 5/05* (2013.01); *A61B 5/062* (2013.01); *A61B 5/6851* (2013.01); *A61B 5/6852* (2013.01); *A61B 34/20* (2016.02); *A61B 90/36* (2016.02); *A61B 90/39* (2016.02); *G01K 1/26* (2013.01); *G01K 13/04* (2013.01); *G01L 9/0001* (2013.01); *G01L 9/007* (2013.01); *A61B 5/02158* (2013.01); *A61B 2034/2051* (2016.02); *A61B 2034/2072* (2016.02); *A61B 2090/3958* (2016.02); *A61B 2090/3966* (2016.02); *A61B 2562/0223* (2013.01)

(58) Field of Classification Search
    CPC .. A61B 1/00158; A61B 5/02152; G01K 7/36; G01L 9/007
    See application file for complete search history.

(56) References Cited

U.S. PATENT DOCUMENTS

| | | | | |
|---|---|---|---|---|
| 4,254,395 A * | 3/1981 | Herden | ................... | G01L 9/007 338/41 |
| 4,340,877 A * | 7/1982 | Herden | ................... | G01L 9/14 338/42 |
| 4,411,261 A * | 10/1983 | Finney | ................... | A61F 2/26 600/40 |
| 4,523,482 A * | 6/1985 | Barkhoudarian | ....... | G01L 3/103 73/862.336 |
| 4,922,197 A * | 5/1990 | Juds | ...................... | G01B 7/023 324/207.21 |
| 4,936,148 A * | 6/1990 | Shaw | ........................ | G01L 9/14 73/728 |
| 4,938,068 A * | 7/1990 | Clements | .............. | G01L 9/0013 73/DIG. 1 |
| 5,195,377 A * | 3/1993 | Garshelis | ................ | G01L 1/125 73/779 |
| 5,542,293 A * | 8/1996 | Tsuda | .................. | B60C 23/0425 73/146.4 |
| 5,627,465 A * | 5/1997 | Alfors | ...................... | G01B 7/31 324/202 |
| 6,453,185 B1 * | 9/2002 | O'Keefe | ................ | A61B 5/031 600/383 |
| 6,779,409 B1 * | 8/2004 | Kwun | ..................... | G01L 3/102 73/862.333 |
| 6,854,335 B1 * | 2/2005 | Burns | ................ | B60C 23/0425 73/728 |
| 7,446,525 B2 * | 11/2008 | Pullini | ............... | B60C 23/0425 324/207.21 |
| 10,010,251 B2 | 7/2018 | Manstrom | | |
| 10,066,964 B2 * | 9/2018 | Sirohiwala | .............. | H01F 7/021 |
| 10,323,958 B2 * | 6/2019 | Kranz | ..................... | G01B 7/003 |
| 10,335,042 B2 * | 7/2019 | Schoenle | ................. | A61B 8/12 |
| 10,499,817 B2 | 12/2019 | Gregorich | | |
| 2002/0000228 A1 * | 1/2002 | Schoeb | ................. | F16C 32/044 128/204.19 |
| 2003/0130615 A1 * | 7/2003 | Tom | ..................... | A61B 5/6885 604/67 |
| 2003/0136417 A1 | 7/2003 | Fonseca | | |
| 2004/0112138 A1 * | 6/2004 | Knirck | .................... | G01L 1/205 73/754 |
| 2005/0174109 A1 | 8/2005 | Pullini | | |
| 2006/0006994 A1 * | 1/2006 | Moser | .................. | B60C 23/043 340/448 |
| 2006/0030772 A1 * | 2/2006 | Hyde | ....................... | A61B 5/06 604/540 |
| 2007/0179333 A1 * | 8/2007 | Bove | ........................ | A61N 2/06 600/15 |
| 2007/0236213 A1 * | 10/2007 | Paden | ...................... | A61B 3/16 324/228 |
| 2008/0184799 A1 * | 8/2008 | Phan Le | ............... | G01P 15/105 73/514.31 |
| 2009/0134721 A1 * | 5/2009 | Zimmerling | ........... | H02K 35/02 310/15 |
| 2009/0224837 A1 | 9/2009 | Joy | | |
| 2010/0058583 A1 * | 3/2010 | Cros | ...................... | A61B 5/0215 257/E21.09 |
| 2010/0265176 A1 * | 10/2010 | Olsson | .................... | G06F 3/016 345/161 |
| 2011/0066098 A1 * | 3/2011 | Stergiopulos | ....... | A61F 9/00781 604/9 |
| 2011/0232392 A1 * | 9/2011 | Suess | ...................... | G01L 1/125 73/779 |
| 2015/0126829 A1 | 5/2015 | Bernstein | | |
| 2016/0011012 A1 * | 1/2016 | Goodbread | .......... | G01N 29/036 73/64.53 |
| 2017/0234741 A1 | 8/2017 | Erickson | | |
| 2018/0021497 A1 * | 1/2018 | Nunez | ................... | A61M 60/17 600/16 |
| 2018/0046249 A1 * | 2/2018 | Peretz | ..................... | G06F 3/016 |
| 2021/0244305 A1 * | 8/2021 | Gleich | ................... | A61B 90/39 |

OTHER PUBLICATIONS

Tan, et al: "Design, Fabrication, and Implementation of a Wireless, Passive Implantable Pressure Sensor Based on Magnetic Higher-Order Harmonic Fields", Biosensors 2011, 1, 134-152.

\* cited by examiner

PRESSURE SENSING UNIT, SYSTEM AND METHOD FOR REMOTE PRESSURE SENSING

CROSS REFERENCE TO RELATED APPLICATIONS

This application is the U.S. National Phase application under 35 U.S.C. § 371 of International Application No. PCT/EP2019/065090 filed Jun. 11, 2019, which claims the benefit of European Patent Application Number 18178783.9 filed Jun. 20, 2018. These applications are hereby incorporated by reference herein.

FIELD OF THE INVENTION

This invention relates to pressure sensing, and in particular using a remote and passive pressure sensor for example an implanted pressure sensor.

BACKGROUND OF THE INVENTION

The measurement of blood pressure is important in medicine.

In recent decades, for example, wire-based measurement of blood pressure in the coronaries has become an important tool for assessing the severity of stenosis, for example in a fractional flow reserve, FFR, procedure. This involves coronary catheterization during which a catheter is inserted into the femoral (groin) or radial arteries (wrist) using a sheath and guidewire. FFR uses a small sensor on the tip of the wire to measure pressure, temperature and flow to determine the exact severity of the lesion. This is done during maximal blood flow (hyperemia), which can be induced by injecting suitable pharmaceutical products.

Implanted pulmonary pressure sensors have also been proposed and commercialized for measuring right-heart pressure.

The main problem of the FFR procedure is the lack of a true wireless solution to facilitate a swift workflow. In addition, it would be desirable to have more than one sensor on the guide-wire and it would be beneficial if a precise localization of the sensors was possible.

In the case of other applications, e.g. pressure monitoring in aneurysms, a sufficiently small wireless solution is also still lacking.

One wireless approach involves providing induction coils as part of the implanted sensor, for establishing communication to an external controller. These coils need to have about a 1 mm diameter and for this reason they are too large for some delivery types and implantation sites.

Ultrasound based sensors have also been proposed, but they do not work in every body location (e.g. lung) and the readout needs direct skin contact, which is often not practical.

The article "Design, Fabrication, and Implementation of a Wireless Passive Implantable Pressure Sensor Based on Magnetic Higher-Order Harmonic Fields" of Ee Lim Tan et. al., Biosensors 2011, 1, 134-152, ISSN 2079-6374 discloses a pressure sensor using a magnetically soft material and a permanent magnet strip to create a magnetic signature which depends on the separation of the two elements. The separation is changed by the pressure being sensed. This produces a weak signal (as a result of a demagnetization factor) and hence is not easy to miniaturize.

There remains a need for a miniature wireless solution for remote passive pressure measurement.

SUMMARY OF THE INVENTION

The invention is defined by the claims.

According to examples in accordance with an aspect of the invention, there is provided a wireless pressure sensing unit, comprising:

a closed cavity, wherein the cavity comprises at least one membrane forming an outer wall portion of the cavity;

a first permanent magnet inside the cavity and coupled to the at least one membrane; and a second permanent magnet inside the cavity, wherein at least one of the first and second permanent magnets can perform a rotational movement about a rotation axis and wherein at least a part of the magnetic moment is oriented perpendicular to the rotation axis.

This pressure sensing unit comprises two permanent magnets, and at least one is movable to implement a rotation. The separation distance between the two permanent magnets is a function of the external pressure (i.e. external to the cavity), since this deforms the membrane which in turn moves the two permanent magnets relative to each other. There may be only one membrane to which the first permanent magnet is coupled, but there may instead two membranes each coupled to a respective permanent magnet.

In all cases, the separation distance is changed by deflection of the membranes and this influences the way their magnetic fields interact and hence influences a magneto-mechanical resonant frequency. The pressure can thus be sensed based on the resonant frequency components in a detected magnetic field, in particular caused by rotational oscillatory movements of the non-fixed permanent magnet.

This sensing approach, based on a rotational oscillation, provides highly sensitive operation as well as enabling the unit to be miniaturized for example for use as an implanted sensor, with remote read-out.

In one arrangement, one of the first and second permanent magnets can perform a rotational movement and the other of the first and second permanent magnets is fixed. This means there is only one movable part. It is however possible for both permanent magnets to be able to move, and the resulting influence on the generated magnetic field will still be detectable.

The two permanent magnets are for example aligned with their poles in opposite directions, namely in a stable state, which is then disturbed by an external field. This means the two magnets are attracted to each other.

The movable permanent magnet performs rotational oscillations in the magnetic field of the other permanent magnet. The local magnetic field depends on the proximity of the magnets which then determines the resonance frequency of the oscillation. Note that this pressure sensing unit is only the remote part of an overall system. Excitation into resonance and readout is achieved by a separate remote unit.

The membrane is for example made of an elastomer or a patterned metal sheet. It deforms in response to the external pressure, thereby changing the separation distance.

The cavity may be a cylinder, and the membrane forms one end of the cylinder, or there may be a membrane at each end of the cylinder.

A cylinder is particularly suitable for a miniature sensor for example for passing along a conduit such as a blood vessel.

The at least one of the first and second permanent magnets may comprise a rotationally symmetric shape such as a sphere or cylinder. In this way the rotation does not induce a physical vibration. Both permanent magnets may have the same shape, or they may be different. A spherical magnet is preferred as it is easy to produce to the desired size and tolerance.

The at least one of the first and second permanent magnets fits inside the cylinder with a surrounding spacing so that it oscillates in space without frictional surface contact. The at least one of the first and second permanent magnets is constrained to rotate as a result of the attraction forces between the two magnets. Thus, the movement of the permanent magnets does not require the unit to occupy any additional space.

The second permanent magnet is for example coupled to the cavity by a fixed coupling, and the first permanent magnet is coupled to the membrane by a wire or thread.

This wire or thread is for example kept taut by the magnetic force of attraction between the two permanent magnets. This force is for example one or more orders of magnitude larger than a gravitational force. Thus, the sensor unit can operate with any orientation. The wire or thread will be kept under an extensional load by the magnetic forces. These forces also center the at least one of the first and second permanent magnets and thus ensure rotation about a fixed axis.

The first permanent magnet is for example glued into the cylinder whereas the second permanent magnet is suspended by the wire or thread. The wire or thread provides a fixed distance between the membrane and the second permanent magnet because it is kept taut, but it can twist to allow the resonant oscillations. Note that in an alternative arrangement, the permanent magnet associated with the membrane may be fixed and the permanent magnet associated with the cavity may be free to rotate.

The unit for example has an outer shape such that it fits into a cylinder of diameter 1 mm, for example of diameter 0.5 mm, for example of diameter 0.3 mm.

These levels of miniaturization make the device particularly suitable for implantation into the body.

The invention also provides a pressure sensing system, comprising:
a pressure sensing unit as defined above;
an excitation coil arrangement for wirelessly inducing a resonant rotational oscillation of the at least one of the first and second permanent magnets by generating a magnetic field.

The overall system has an external excitation system. It may be a coil surrounding the pressure sensing unit (e.g. surround the body part of a subject in which the pressure sensing unit is implanted) or just for placement against the body, or coils for placement on each side of the pressure sensing unit. The location of an implanted pressure sensing unit may for example be determined by X-ray, but it may instead be determined based on the sensing itself.

The external coil (or coils) generates low strength oscillating magnetic fields to excite the rotational mechanical oscillation.

The system may further comprise a controller, adapted to:
control the excitation coil arrangement to induce and sustain resonant oscillation of the other one of the first and second permanent magnets; and
measure a magnetic field which is altered by the resonant oscillation.

The resonant oscillations can thus be detected, and their frequency correlates with the sensed pressure.

The controller may be adapted to control the excitation coil arrangement to induce and sustain resonant oscillation by applying a discontinuous external magnetic field. In this way, the resonant oscillation is sustained, to overcome frictional and other losses that otherwise damp the oscillations.

The controller may be adapted to measure a magnetic field between the active periods of the discontinuous external field or during the active periods of the discontinuous external field or during a continuous external field. There may thus be a repeating sequence of excitation and measurement or else simultaneous excitation and measurement.

The excitation coil arrangement may comprise at least 3 non-collinear coils for inducing and sustaining resonant oscillation and at least 3 non-collinear coils for measuring the magnetic field. The use of multiple coils in this way ensures that any orientation of the pressure sensing unit, relative to the excitation field, can be tolerated.

The controller may be adapted to use the same coil or coils for inducing the resonant oscillation as for measuring the magnetic field. This provides a low cost set of hardware. Of course, separate coils may be used if desired.

The system may comprise multiple pressuring sensing units, each with different resonant frequencies.

These may be used to measure pressures at multiple locations, and the different locations can be identified based on the known range of resonant frequencies they produce.

The invention also provides a catheter or guidewire system, comprising:
a catheter or guidewire; and
a system as defined above, wherein the pressure sensor unit is provided along the catheter or guidewire.

There may be one pressure sensing unit at the tip or there may be multiple pressure sensing units along the length of the catheter or guidewire.

The invention also provides a pressure sensing method, comprising:
using an excitation coil arrangement to wirelessly excite a pressure sensing unit into a resonant oscillation, wherein the pressure sensing unit comprises:
  a closed cavity wherein the cavity comprises at least one membrane forming an outer wall portion of the cavity;
  a first permanent magnet inside the cavity and coupled to the at least one membrane;
  a second permanent magnet inside the cavity, wherein at least one of the first and second permanent magnets can perform a rotational movement about a rotation axis, wherein at least a part of the magnetic moment is oriented perpendicular to the rotation axis, wherein the at least one of the permanent magnets is excited into the resonant oscillation;
measure a magnetic field which is altered by the resonant oscillation; and
determine a pressure from the frequency of alteration of the measured magnetic field.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
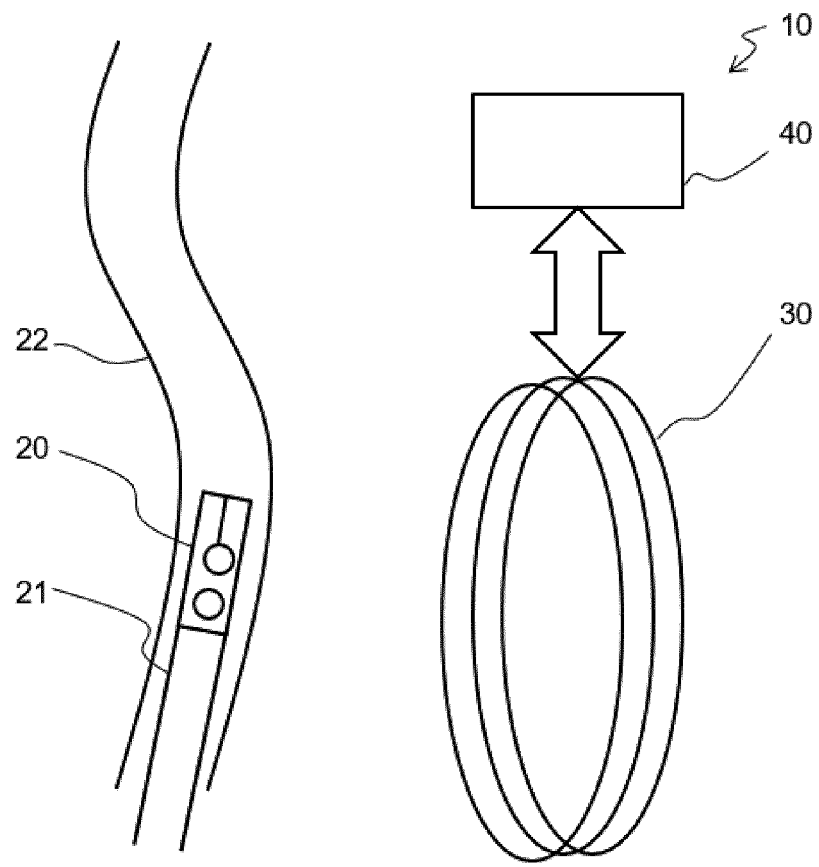
FIG. 1 shows a pressure sensing system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a wireless pressure sensing unit which comprises two permanent magnets. At least one is free to oscillate with a rotational movement. The oscillation takes place at a resonance frequency which is a function of the sensed pressure, which pressure influences the spacing between the two permanent magnets. This oscillation frequency can be sensed remotely.

FIG. 1 shows a pressure sensing system 10 comprising a pressure sensing unit 20 which senses a local pressure. The pressure sensing unit 20 is wireless and needs no local source of power. It modulates a generated magnetic field in dependence on the pressure sensed. In particular, it enters a state of mechanical resonance oscillation induced by an external electromagnetic field, and this mechanical resonance can be detected by the effect it has on the magnetic field produced by the sensing unit 20 itself. The pressure sensing unit 20 in this example is at the end of a medical intervention shaft 21, i.e. a catheter or guidewire. It may be any position along the shaft or indeed there may be multiple pressure sensing units along the shaft. The pressure sensing unit may instead be a permanently implanted device, for example part of a stent or medical coil.

The system 10 has an excitation coil arrangement 30 for wirelessly inducing the magnetically induced mechanical resonance.

The excitation coil arrangement may be a single coil (by which is meant one or multiple individual turns but all parallel to each other and around a common axis) or it may be multiple coils with parallel, or non-parallel orientations.

FIG. 1 shows in schematic form the excitation coil arrangement 30 to the side of the pressure sensing unit 20. It may instead surround the pressure sensing unit (e.g. surround the body part of a subject in which the pressure sensing unit is implanted). There may be more than one coil, whereas all the coils are arranged and wound in the same plane forming an array. This coil array may be placed below the patient (the patient for example lies on a flat structure). However, there are many ways to arrange the excitation coil arrangement. Another example is to use coils wound on soft magnetic (ferrite) rods placed at the side(s) of the patient.

The required size of the external coil depends on the technology used. The total diameter of a flat coil array may for example be of the same order of magnitude as the maximum measurement distance. Smaller coils need more power and possibly a lower noise receive amplifier. Coils utilizing a soft magnetic material core can be much smaller in diameter. By way of example, each coil may have a diameter of around a tenth of the maximum distance.

A controller 40 is used to drive the excitation coil arrangement 30 to generate an alternating electromagnetic field. In addition, the controller analyzes a detected magnetic field, in particular to detect a mechanical resonance frequency of the pressure sensing unit, which depends on the local pressure being sensed.

In a typical (but not the only possible) use, the pressure sensing unit 20 is implanted into a vessel 22 or an organ of a subject. The location may be identified and tracked by imaging systems such as X-ray to place the pressure sensing unit at a desired location. The excitation coil arrangement can be positioned at the appropriate location. Alternatively, the pressure sensing unit can be brought to the desired location based on the detection by the external coil 30 the location of the magnetic field generated by the pressure sensing unit 20.

The controller 40 uses the external coil 30 (or coils) to generate low strength oscillating fields to excite the resonance but also to sustain resonant oscillations. In the example of FIG. 1, the same excitation coil arrangement is used to measure the magnetic field which is altered by the resonant oscillation. Alternatively, a separate coil or coils may be used for detection of the varying magnetic field generated by the oscillations.

The controller may induce and sustain resonant oscillation by applying a pulsed alternating field and it may measure the magnetic field between the pulses. There is thus a sequence of excitation and measurement.

Figure 2:
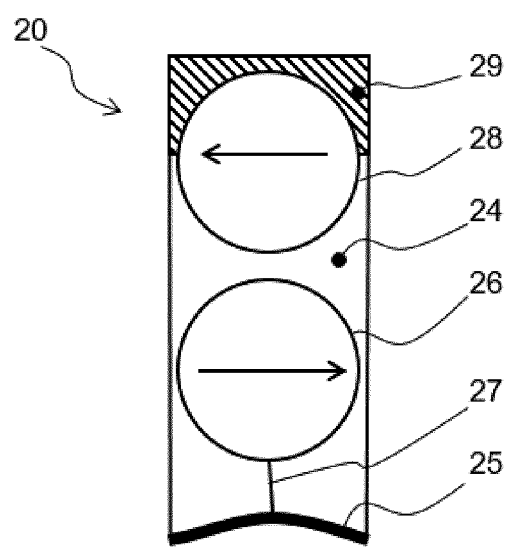
FIG. 2 shows the pressure sensing unit in more detail.

FIG. 2 shows an example of the pressure sensing unit 20 in more detail.

It comprises a closed cavity 24 formed by a metal or polymer casing. A deformable membrane 25 forms an outer wall portion of the cavity. It may for example be an elastomer or structured metal foil. The cavity is filled with gas (e.g. air) or evacuated.

In the example shown, the cavity is a cylinder, and the membrane 25 forms an end wall. In an alternative example, both end walls may be formed by a membrane, and the two membranes move inwardly towards each other in response to an increase in external pressure.

The outer diameter of the cylinder and hence of the sensing unit can below 0.3 mm for example as small as 0.2 mm, more generally below 1 mm, and preferably below 0.5 mm. More generally (and regardless of the specific shape) the pressure sensing unit may fit into a cylinder of internal diameter as listed above. The pressure sensing unit can then be integrated into a permanent implant such as a stent or aneurysm coiling, or a temporary implant such as a guidewire or catheter, or it could be delivered independently such as via the blood stream to enter the lung.

The pressure sensing unit for example has a length in the range 1 mm to 5 mm. A first permanent magnet 26 is coupled to the membrane by an elongate structure 27 (e.g. wire or thread). A second permanent magnet 28 is coupled to the inside of the cavity, in particular to the closed end opposite the membrane 25. The second permanent magnet is attached for example by glue 29. Thus, in this particular example, the second permanent magnet is static (relative to the fixed parts of the cavity).

The permanent magnets may be spheres, and at least the first permanent magnet 26 fits inside the cavity with a spacing all around. The fixed second permanent magnet 28 together with the elongate structure 27 center the rotating first permanent magnet 26 automatically in the device. In this way, the rotating magnet never touches the inside of the casing. This enables a high quality factor oscillation.

The rotation axis corresponds to the elongate axis of the wire or thread, which runs along the length direction of the cavity. At least a part of the magnetic moment of the movable permanent magnet 26 is oriented perpendicular to the rotation axis. Thus, a magnetic force experienced by the magnet 26 may induce a rotational torque about the rotation axis. In the example shown, the permanent magnets are dipole magnets, with their magnetic moments fully perpendicular to the rotation axis. The magnetic forces cause the magnets to align along the rotation axis, with their magnetic moments in opposite directions, as shown. The attraction between the permanent magnets keeps the elongate structure 27 taut, therefore the elongate structure may be wire or thread from a material exhibiting compliance.

Other magnet shapes may be used, such as cylinder magnets or indeed other shapes. The movable first magnet preferably has a rotationally symmetric shape about the axis of rotation so that the rotation is balanced. An advantage of the spherical magnets shown is that they can be easily manufactured to high precision and are therefore easily available.

The two permanent magnets do not need to be of the same size or shape or type. Basically, the fixed permanent magnet is used to create a static field, with which the field of the moving permanent magnet interacts. The moving permanent magnet is used to create a rotating oscillation and hence a rotating field with interacts with the stationary field of the fixed permanent magnet.

The two permanent magnets are aligned oppositely, i.e. with north-south and south-north pole pairs adjacent each other. The rotational stiffness of the elongate structure (wire or thread) can be chosen to be low in comparison to the torsion due to the magnetic field. There is a strong attraction between the two magnets and therefore a stress in the wire or thread direction is imposed on the wire or thread. The magnetic force is typically several hundred times the gravitational force. Thus, the wire or thread does not need significant rigidity and can for example be a very thin UHMWPE (Ultra High Molecular Weight Polyethylene) thread. It also means the sensor unit can operated with any orientation, since the effect of gravity on the sensor readings is negligible.

In the example shown, the second permanent magnet 28 is coupled with a fixed, static, angular position and the first permanent magnet 26 is coupled with an elongate structure exhibiting compliance (e.g. wire or thread) that allows angular rotational movement.

The separation distance between the two magnets is a function of the external pressure (i.e. external to the cavity), since this deforms the membrane 25 which in turn moves the two permanent magnets relative to each other. The distance between the permanent magnet 26 and the membrane 25 is fixed by the elongate structure (wire or thread) which is kept taut by the magnetic attraction between the two magnets.

The permanent magnet 26 is able to rotate, in particular about the axis defined by the wire or thread 27. The wire or thread may be sufficiently thin that the torques on the permanent magnet 26 due to twisting of the wire or thread may be smaller than the torques experienced due to magnetic forces. This is not however essential. A stiffer wire or thread will shift the resonant frequency of oscillation to a higher value and therefore the recorded signal will be at a higher frequency, which may be easier to process. However, a higher frequency signal will give a lower frequency change per unit pressure change.

The resonant frequency is roughly inversely proportional to the linear dimension of the resonating body. Therefore, for a 1 mm diameter device, a resonant frequency will be of around 500 Hz, whereas for a 0.2 mm device the frequency will be around 2.5 kHz.

A resonance rotational oscillation is started by suitable electromagnetic impulses generated by the excitation coil arrangement 30.

An excitation signal may be used with a frequency selected which depends on the resonance frequency if approximately known in advance. Alternatively, the oscillation may be started with a single short excitation pulse. This starts an oscillation which can be recorded. The resonance frequency can then be measured, and the next pulses can then be timed in a way that the amplitude of oscillation increases.

An alternative approach is to start the oscillation using a long train of pulses that exhibit a narrow frequency spectrum. The center frequency may then be varied until the resonance is sufficiently well met to receive a signal from the sensor. The frequency can then be tracked. By varying the length of the pulse train, the spectral selectivity can be varied. The advantage of a long (spectral selective) pulse train is that it requires a lower magnetic field amplitude to set the sensor into resonance. Therefore, it requires a lower technical effort on the send/receive system and/or can find a sensor at a larger distance from the coil.

The drawback of the use of spectrally selective pulses is that it will on average take longer to find the sensor.

A series of pulses may thus be used to maintain resonant oscillation. This series of pulses then induces and sustains resonant oscillation with a discontinuous external magnetic field. The pulses used to sustain oscillation for example have a duration of at least ⅛ of the oscillation period in length i.e. 0.25 ms for a 1 mm sphere (500 Hz) and 0.05 ms for a 0.2 mm sphere (2.5 kHz). The pulses could be even shorter by increasing the amplitude.

A lifetime of the oscillation may for example be of the order of seconds, such as 2 seconds. Therefore the maximum separation of the excitation pulses is approximately 1 second. In principle, the lifetime could be much longer, of tens or even hundreds of seconds, and the gap between excitation pulses may be adapted accordingly, with a maximum gap of the order of half of the oscillation lifetime. It is preferred however to implement many excitations per second to maintain a resonant response with substantially constant amplitude.

By way of example, it may be desired to measure the pressure about 10 times per second, so the use of 10 excitation trains per second is appropriate. Smaller devices may for example be desired to perform 50 or more measurements per second, and it would then be preferred to provide a larger number of excitations per second. There may be an excitation for each signal read out, so that the readout is carried out at the same point in the lifetime of the oscillation, but this is not required. There may be any ratio between the period between excitations and the period between signal read out.

The use of a discontinuous excitation signal enables time sequential excitation and read out. In this way, once the rotational oscillation of the first permanent magnet 26 is started, the subsequent field pulses are timed in a way to enhance the oscillation. Between the sent excitation pulses, the oscillating magnetic field generated by the sensor unit is measured.

However, simultaneous excitation and read out is also possible in which case a continuous excitation signal may be used. This requires a more complex receiver system.

In particular, to facilitate simultaneous signal measurement while providing excitation, the signal generated at the receiver in response to the excitation signal itself has to be minimized. This can be achieved by a combination of analog subtraction of the transmitted (send) signal at the receiver (e.g. by using a transformer before the receiver in which a part of the send signal is fed) and digital subtraction. In the digital subtraction step, the residual send signal at the receiver is first characterized and then digitally subtracted from the digitized received signal.

Thus, there are various ways to set the sensor into resonant oscillation.

The measurement of the resonant frequency in the magnetic field generated by the pair of magnets, which depends on the mechanical rotation of the movable magnet (or the rotation of both magnets as a rotating system if both magnets are movable), may also be carried out in various ways. The measurement may be implemented by the same excitation coil arrangement as mentioned above or by a separate receive system. The receive system may utilize magnetic field sensors other than simple coils, such as fluxgate magnetometers, but coils can already provide the required sensitivity.

The separation distance between the two permanent magnets influences the mechanical response of the movable permanent magnet to the external field as explained above. In particular, the closer the movable permanent magnet is to the fixed permanent magnet, the greater the force provided by the magnetic field of the fixed permanent magnet to align the movable permanent magnet. This force results in a higher resonant frequency of the mechanical resonance.

The interaction between the two magnetic fields is detectable, and since there is a dependency on the mechanical movement of the movable permanent magnet, the resonance frequency can be detected.

Figure 3:
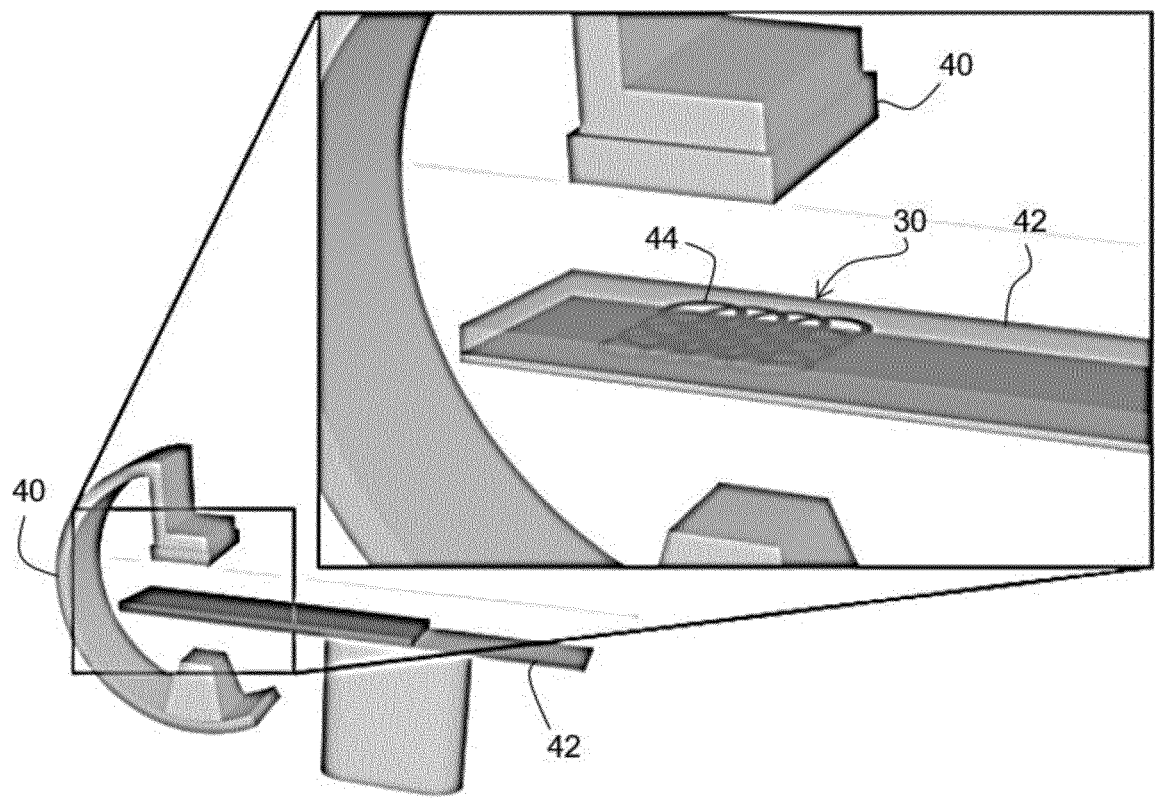
FIG. 3 shows an apparatus combining the excitation coil arrangement, an X-ray system and a patient bench.

FIG. 3 shows an apparatus combining the excitation coil arrangement 30, an imaging system 40 (e.g. X-ray C-arm) and a patient bench 42. The pressure sensing unit is an implanted sensor in the patient, who lies on the bench. The imaging system, in this case an X-ray C-arm, may be used to locate the pressure sensing unit.

The excitation coil arrangement 30 comprises an array of overlapping substantially planar coils 44 forming a flat coil array integrated into the patient bench 42. The coils are for example made from aluminum with a total thickness on the scale of mm, for example below 2 mm thickness. The x-ray absorption from the X-ray system is low.

The coils may comprise single loops or flat spirals cut from a metal sheet. As mentioned above, the individual coils as well as the size of the overall coil arrangement, are designed taking into account the required magnetic field at the sensor unit and the maximum distance to the sensor unit.

Figure 4:
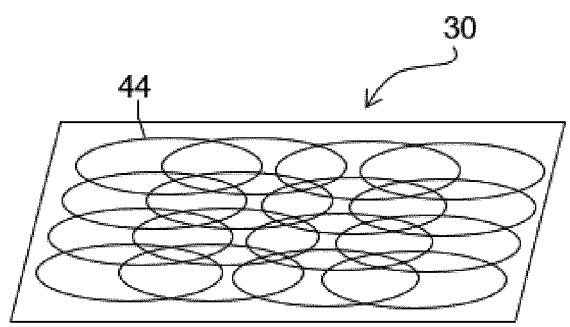
FIG. 4 shows a first example of possible excitation coil arrangement.

FIG. 4 shows a first example of possible excitation coil arrangement which represents more clearly the arrangement shown in FIG. 3. It comprises an array of flat coils 44.

Figure 5:
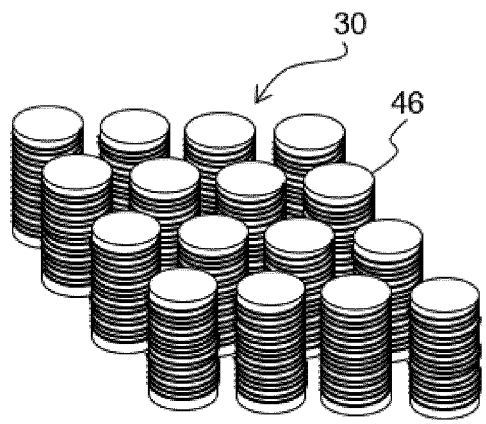
FIG. 5 shows a second example of possible excitation coil arrangement.

FIG. 5 shows a second example of possible excitation coil arrangement comprising an array of cylindrical coils 46. They may comprise air core coils or coils with a ferrite core.

Figure 6:
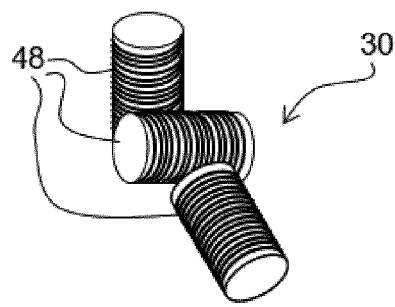
FIG. 6 shows a third example of possible excitation coil arrangement.

FIG. 6 shows a third example of possible excitation coil arrangement with three non-collinear coils 48. In the example shown, the magnetic moments of the three coils are mutually perpendicular to each other. This improves the freedom of the pressure sensing unit to have any directional orientation relative to the excitation coil arrangement.

The excitation system and the receiving system may both have at least three non-collinear field generators and receivers. However, for many applications, e.g. implanted sensors that are only read out from time to time, a one axis system may be sufficient, especially if it can be oriented freely.

Thus, it will be seen that there are many possible designs for the excitation coil arrangement, and these will be apparent to those skilled in the art.

The system can be extended to include multiple sensor units. This may enable sensing at multiple locations, and it also may provide a way to reconstruct the position of the sensor unit, using the relative amplitudes in the receiving systems or the relative amplitudes in the excitation systems needed to maintain a certain oscillation amplitude.

Multiple sensors may be operated in parallel if they are tuned to different resonance frequencies, e.g. by using different distances between the permanent magnets or different magnetic properties in the sensors.

A shared coil system may be used, for example be ensuring timing and/or shaping of the excitation pulses in such a way that all sensors increase their energy content. Ideally, the range of possible resonant frequencies for the different sensor units then do not overlap so that the receiving system with excitation and receiving coils located at different positions can distinguish between the sensors.

In the example above, the membrane is attached to the movable permanent magnet. Of course, the permanent magnet associated with the membrane may instead by fixed relative to the membrane and the permanent magnet associated with the cavity may be free to rotate. As mentioned above, there may be two membranes, each coupled to one of the permanent magnets so that they both move towards each other in the presence of an external pressure. Only one of the two permanent magnets may be coupled to its respective membrane in such a way as to enable rotational movement, or else both may be coupled to allow rotational movement, i.e. they may both be connected by an elongate structure (a wire or thread) to their respective membrane.

The variation of the resonant frequency in response to the full pressure range for which the sensor is designed for example, corresponds to a frequency variation with a factor 2. The wire or thread will also contribute to the torque encountered during oscillation, so the frequency response may be more significant depending on the design of the wire or thread.

The desired pressure range is for example from about 800 mBar (80 kPa, absolute pressure) to about 1300 mBar (0.13 MPa, absolute pressure). The low end for example corresponds to a low blood pressure at high altitudes (e.g. Mexico City). There may if desired be two (or more) product designs, one for normal altitudes and one for high altitudes to narrow the pressure range and hence increase sensitivity.

The pressure sensing unit may be applied to a catheter or a guidewire, or it may be used in other application such as pulmonary artery pressure sensors, sensors on implanted valves, pressure sensors at stents or medical coils.

Figure 7:
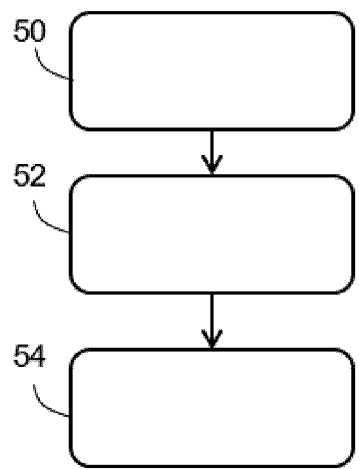
FIG. 7 shows a pressure sensing method.

FIG. 7 shows a pressure sensing method, comprising:

in step 50, using an excitation coil arrangement to wirelessly excite a pressure sensing unit as described above into a resonant oscillation;

in step 52, measuring a magnetic field which is altered by the resonant oscillation; and in step 54, determining a pressure from the frequency of alteration of the measured magnetic field.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A pressure sensing unit, comprising:
   a structure defining a closed cavity, wherein the structure comprises at least one membrane forming an outer wall portion of the closed cavity, and wherein the structure is configured to be implanted within a human subject;
   a first permanent magnet inside the closed cavity and coupled to the at least one membrane; and
   a second permanent magnet inside the closed cavity,
   wherein the second permanent magnet is coupled to the structure by a fixed coupling, wherein the fixed coupling prevents rotational movement of the second permanent magnet with respect to the structure; and
   an elongate structure,
   wherein the first permanent magnet is coupled to the at least one membrane by the elongate structure, wherein the elongate structure allows rotational movement of the first permanent magnet with respect to the structure.

2. The unit as claimed in claim 1, wherein the elongate structure comprises a wire or thread.

3. The unit as claimed in claim 1, wherein the membrane is made from an elastomer or a patterned metal sheet.

4. The unit as claimed in claim 1, wherein the structure has a shape of a cylinder, and;
   wherein there is one membrane which forms one end of the cylinder; or
   there is a respective membrane forming each end of the cylinder.

5. The unit as claimed in claim 4, wherein the first permanent magnet has a rotationally symmetric shape.

6. The unit as claimed in claim 1, wherein an interior of the closed cavity, except for the first and second permanent magnets and the elongate structure is filled with air or holds a vacuum.

7. The unit as claimed in claim 1, wherein the unit has an outer diameter of no more than 0.3 mm.

8. A pressure sensing system, comprising:
   a pressure sensing unit of claim 1;
   an excitation coil arrangement having a plurality of coils for wirelessly inducing a resonant rotational oscillation of said first permanent magnet by generating a magnetic field.

9. A system as claimed in claim 8, further comprising a controller, wherein the controller is adapted to:
   control the excitation coil arrangement to induce and sustain resonant oscillation of the said first permanent magnet; and
   measure a magnetic field which is altered by the resonant oscillation.

10. The system as claimed in claim 9, wherein the controller is adapted to control the excitation coil arrangement to induce and sustain the resonant oscillation by applying a discontinuous external magnetic field.

11. The system as claimed in claim 10, wherein the controller is adapted to measure a magnetic field between active periods of the discontinuous external field.

12. The system as claimed in claim 8, wherein the controller is adapted to use a same coil or ones of the cods for inducing and sustaining the resonant oscillation as for measuring the magnetic field.

13. The system as claimed in claim 8, comprising multiple pressuring sensing units, each with different resonant frequencies.

14. A catheter or guidewire system, comprising:
   a catheter or guidewire; and
   a system as claimed in claim 8, wherein the pressure sensor unit is provided along the catheter or guidewire.

15. A pressure sensing method, comprising:
   using an excitation coil arrangement to wirelessly excite a pressure sensing unit into a resonant oscillation, wherein the pressure sensing unit is implanted into a human subject and comprises:
      a structure defining a dosed cavity, wherein the structure comprises at least one membrane forming an outer wall portion of the dosed cavity;
      a first permanent magnet inside the dosed cavity and coupled to the at least one membrane;
      a second permanent magnet inside the dosed cavity, wherein the second permanent magnet is coupled to the structure by a fixed coupling, wherein the fixed coupling prevents rotational movement of the second permanent magnet with respect to the structure, and wherein the first permanent magnet is coupled to the membrane by an elongate structure, wherein the elongate structure allows rotational movement of the first permanent magnet with respect to the structure, wherein at least a part of magnetic moment between the first and second permanent magnets is oriented perpendicular to a rotation axis of the first permanent magnet, wherein the first permanent magnet is excited into the resonant oscillation;
   measure a magnetic field which is altered by the resonant oscillation; and
   determine a pressure from the frequency of alteration of the measured magnetic field.

16. The unit of claim 1, wherein the elongate structure is only supported by the first permanent magnet and the membrane which forms the outer wall portion of the closed cavity.

17. The unit of claim 1, wherein the elongate structure extends between a first end thereof and a second end thereof, wherein the elongate structure further extends between the first permanent magnet and the membrane which forms the outer wall portion of the closed cavity, and wherein the elongate structure is connected at the first end thereof to the first permanent magnet, and wherein elongate structure is connected at the second end thereof to the membrane which forms the outer wall portion of the closed cavity.

18. The pressure sensing system of claim 8, wherein in the pressure sensing unit, the elongate structure is only supported by the first permanent magnet and the membrane which forms the outer wall portion of the closed cavity.

19. The method of claim 15, wherein the elongate structure is only supported by the first permanent magnet and the membrane which forms the outer wall portion of the closed cavity.

20. The method of claim 15, wherein the elongate structure extends between a first end thereof and a second end thereof, wherein the elongate structure further extends between the first permanent magnet and the membrane which forms the outer wall portion of the dosed cavity, and wherein the elongate structure is connected at the first end thereof to the first permanent magnet, and wherein elongate structure is connected at the second end thereof to the membrane which forms the outer wall portion of the dosed cavity.

\* \* \* \* \*